March 12, 1974 G. DELBARD Plant Pat. 3,519
ROSE PLANT
Filed Oct. 25, 1972
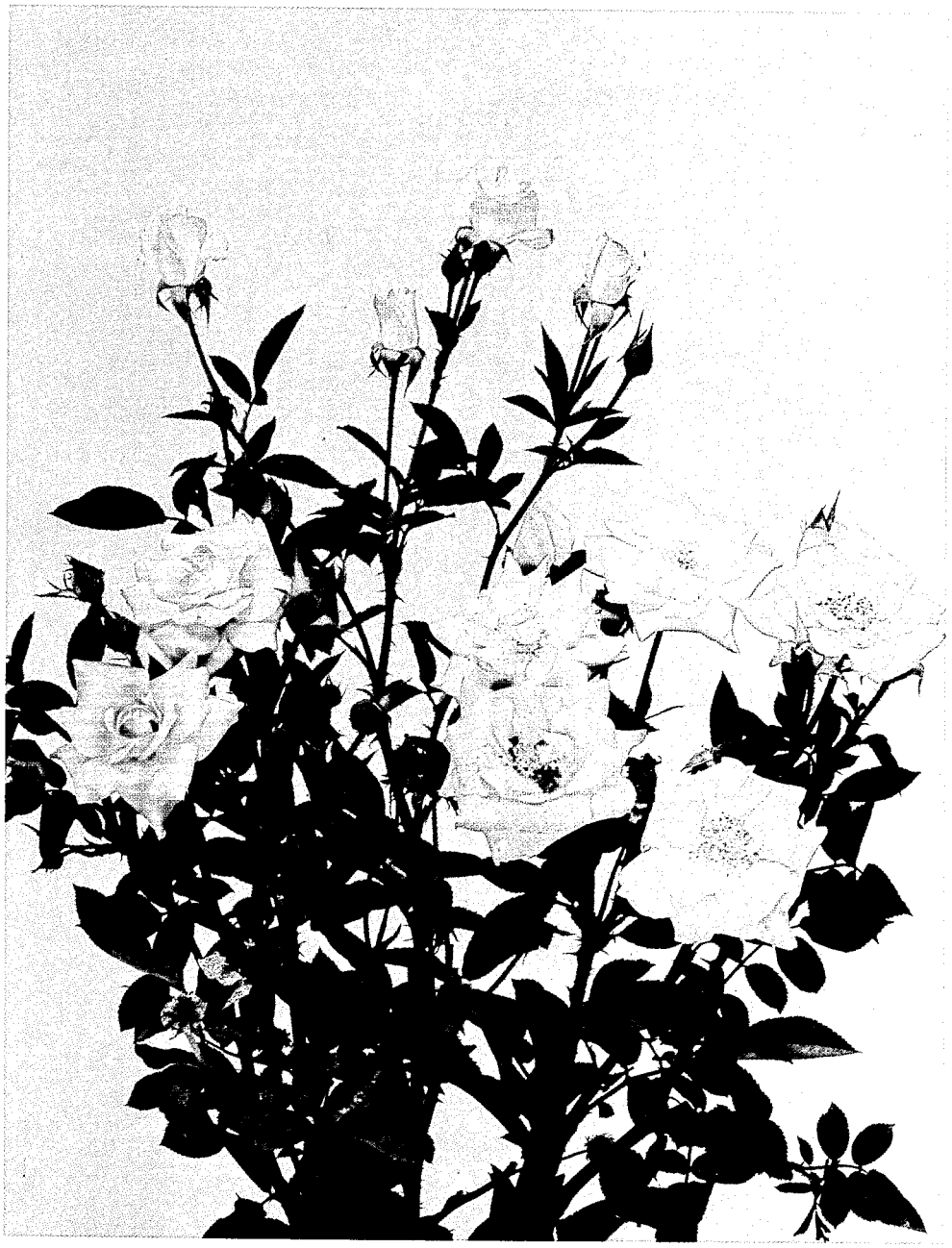

United States Patent Office

Plant Pat. 3,519
Patented Mar. 12, 1974

3,519
ROSE PLANT

Georges Delbard, Paris, France, assignor to Armstrong Nurseries, Inc., Ontario, Calif.

Filed Oct. 25, 1972, Ser. No. 300,647
Int. Cl. A01h 5/00
U.S. Cl. Plt.—22 1 Claim

ABSTRACT OF THE DISCLOSURE

An outdoor bush rose of the floribunda class, with small to medium size semi-glossy leaves, having their lateral margins lifted from the mid-rib. The plant has a tendency to bear a large number of blooms on some of its stems, sometimes even as many as twenty. The general color effect of the newly opened flower is a rather brilliant orange, tending towards a yellowish orange pink as it matures. Pistils range in number from 85 to 140. Fragrance slight, tea to spicy.

This invention relates to a new variety of rose plant of the floribunda class. The plant is a seedling of the outdoor bush type, cultivated primarily for garden decoration. Its hardiness has not yet been completely tested.

The variety was initially propagated by Georges Delbard, at Evry (Essone), France, but the description which follows, and the color plate which illustrates the plant were taken from a plant which was asexually reproduced from the original stock and grown in Ontario, Calif.

The seed parent was "Zambra," Plant Pat. No. 2,140, and the pollen parent was an unnamed and undisseminated seedling (Orange Triomphe × Floradora). The new variety holds its distinguishing characteristics through succeeding propagations by budding.

Although this new variety sometimes bears its blooms singly, usually it bears from three to as many as twenty or more blooms in large regular clusters, on normal, short to medium length stems. The plant blooms abudantly outdoors, and nearly continuously during the growing season. Its fragrance is slight, tea to spicy.

This new variety of rose plant differs from its seed parent "Zambra" in the following particulars:

Whereas the flower of this new cultivar has from 15 to 30 petals plus petaloids, the flowers of Zambra have only 10 to 15 petals plus petaloids.

Although the flowers of both the new cultivar and Zambra are orange, with yellow on the reverse side of the petals, the orange color of Zambra is substantially darker than is true of its new offspring.

Whereas the foliage of Zambra is glossy, the foliage of this new cultivar is non-glossy, or semi-glossy.

The bud of the new cultivar is longer than the bud of Zambra.

The pollen parent of this new cultivar is an unnamed, undisseminated seedling of Orange Triomphe × Floradora, and is not available for comparison.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is from average length to long, slender to average in caliper, erect, with numerous stipitate glands. The color ranges from near Strong Yellow Green, 2.5GY7/10, overlaid with near Strong Red, 5R4/12, to near Moderate Yellow Green, 2.5GY5/5.

Before the calyx breaks, the bud is medium in size, for its class, is medium length to long, pointed and ovoid, with foliaceous appendages on the surface of the bud. As the calyx breaks, the color is between Strong Reddish Orange, 10R6/12, and Dark Reddish Orange, 7.5R4/11, with a lower portion of the exposed petal being near Brilliant Yellow Green, 2.5GY9/8. The inner surface of the sepals carries a fine tomentum. Margins of alternate sepals are lined with a fine tomentum, and margins of others have numerous stipitate glands and some small foliaceous parts which also have stipitate glands on the margins. Apices of the sepals are acuminate. On their outer surface the sepals have stipitate glands.

As the first petal opens, it is average in size, for its class, long, and pointed to urn-shaped. Its color on the outside is near Brilliant Yellow, 5Y9/9, at the base, while the remainder is more vivid than a color between Strong Reddish Orange, 10R6/12, and Strong Yellowish Pink, 10R7/9. On the inside, there is a basal area which is near Vivid Yellow, 5Y8/12, while the remainder is more vivid than a color near Strong Reddish Orange, 10R6/12.

The bud opens up well, and is not retarded, or prevented from opening, by cold, hot, wet, or dry weather.

BLOOM

The size of the bloom when fully open is from 2¼ inches to 3 inches in diameter, which is average for this class. The petalage is double, with from 15 to 30 petals, plus 3 to 10 petaloids arranged regularly. The petal count may vary considerably from flower to flower on the same plant, and even at the same time of year. The blooms are high centered at first, some remaining high centered, others becoming open.

At first the petals remain somewhat cupped, with tips reflexed outward, becoming later at maturity more loosely cupped to flat, with tips reflexed outward. Sometimes the inside petals tend to remain cupped, with tips rolled inward in hot weather.

The petals are of medium thickness, moderately leathery, with the inside satiny to velvety and the outside slightly shiny to satiny. The outside petals are broadly obovate to cordate, with apex somewhat flattened. The intermediate petals are broadly obovate to obovate, with apex rounded. The inside petals are obovate to irregular. The colors may be modified by being bordered, shaded and/or washed with other colors.

The paragraphs immediately following describe color values observed in a flower newly opened in the month of August. The plant had been grown outdoors, in Ontario, Calif.

The outer surface of the outside petal had a basal area which was near Brilliant Yellow, 5Y9/9, the remainder being between Strong Yellowish Pink, 10R7/9, and Strong Yellowish Pink, 7.5R7/9. The inner surface of the outside petal had a basal area which was the same coloration as on the outer surface, the remainder of the petal being between Strong Orange, 2.5YR7/10, and Strong Yellowish Pink, 7.5R7/9.

The intermediate petal had a basal area, both on the outer surface and the inner surface, which was the same color as that of the outside petal. The remainder of the outer surface was between Strong Orange, 2.5YR7/10, and Strong Yellowish Pink, 10R7/9, while the remainder of the inner surface was between Strong Orange, 2.5YR7/10, and Strong Reddish Orange, 10R6/12.

The outer and inner surfaces of the inside petal had a basal area which was also Brilliant Yellow, 5Y9/9. The remainder of the outer surface of the inside petal was between Strong Orange, 5YR7/11, and Strong Yellowish Pink, 10R7/9. The remainder of the inner surface of the inside petal was between Strong Orange, 2.5YR7/10, and Strong Orange, 2.5YR6/12.

The paragraphs immediately following describe the color values observed in a bloom which had been open for three days, outdoors, in the month of August. The plant had been grown outdoors, in Ontario, Calif.

The outer surface of the outside petal had a basal area somewhat lighter than Brilliant Yellow, 2.5Y9/9, while the remainder was between Strong Yellowish Pink, 10R7/9, and Strong Yellowish Pink, 5R7/9. The inner surface of the outside petal had a basal area slightly lighter than Brilliant Yellow, 2.5Y9/9, the remainder being between Strong Yellowish Pink, 7.5R7/9, and Deep Yellowish Pink, 5R6/11.

The outer surface of the inside petal had a basal area near Brilliant Yellow, 2.5Y9/9, while the remainder ranged from Light Orange, 5YR8/7, to Strong Yellowish Pink, 7.5R7/9. The inner surface of the inside petal had a basal area which was near Brilliant Yellow, 5Y9/9, the remainder being between Strong Yellowish Pink, 7.5R7/9, and Strong Reddish Orange, 10R6/12.

The general color effect of the newly opened flower was a color near but more vivid than Strong Reddish Orange, 10R6/12. After being three days open, the bloom gave a general color effect of between Strong Yellowish Pink, 7.5R7/9, and Strong Reddish Orange, 7.5R6/12.

The petals usually drop off cleanly, although some petaloids, dead peduncles and receptacles may persist.

The flowers are not particularly affected by cold, hot, wet, or dry weather. On the bush in the garden, they may persist for from four to five days in the month of August, in the locality named. Cut roses grown outdoors and kept at living-room temperatures will last from four to five days in the month of August.

REPRODUCTIVE ORGANS

Stamens: There are many stamens arranged regularly about the pistils, a few being tucked in and around protruding ovaries.

Filaments: Short to medium length, being ⅛" to 5/16" long, and near Vivid Yellow, 2.5Y8/12, in color.

Anthers: Small, all open approximately at once. On both the upper and under side, they are near Brilliant Yellow, 5Y9/9, the margins being near Moderate Orange Yellow, 10YR8/10.

Pollen: Somewhat sparse to moderate, and near Strong Orange Yellow, 7.5YR7/11, in color.

Pistils: There are many pistils, averaging 125 in number, but with a wide range of variance (from about 85 to about 140).

Styles: Styles are even to uneven, of average length, thin to average caliper, and loosely bunched.

Stigma: Between Vivid Yellow, 2.5Y8/12, and Brilliant Yellow, 2.5Y9/9, in color.

Ovaries: Both enclosed in and protruding from the calyx.

Hips: This plant does not normally set hips on its own outdoors, at Ontario, Calif.

FOLIAGE

The leaves are compound, with usully from 3 to 7 leaflets. They are from normal quantity to abudant, moderately small to medium size, moderately heavy to somewhat leathery, and semi-glossy. The leaflets are ovate-lanceolate in shape, with apex acute, base obtuse, margin doubly serrate, and with some stipitate glands on terminals of serration. The foliage is uniquely characterized by lateral margins that are lifted from the mid-rib.

The mature foliage displays on its upper surface a coloration somewhere between Moderate Olive Green, 5GY4/3, and Grayish Olive Green, 5GY3/2. The under surface is grayer than a color somewhere between Strong Yellow Green, 2.5GY6/8, and Moderate Yellow Green, 2.5GY5/5.

The young foliage on its upper surface is near Strong Yellow Green, 5GY6/8, almost completely overlaid with near Dark Red, 2.5R3/7. Its under surface is near Strong Yellow Green, 7.5GY6/8, lightly to very heavily overlaid with near Dark Red, 2.5R3/7.

The rachis is light to average in size, its upper side being grooved, with many stipitate glands on the edges, and the under side being moderately prickly, and with many stipitate glands.

The stipules are moderately short to medium-length, medium-width, and with moderately short to medium-length points, turning out at an angle of usually less than 90°.

The plant displays an average resistance to mildew.

The plant is compact in habit, bushy, low growing and upright-spreading, and much branched. It displays a vigorous growth, and has canes of medium caliper.

The main stems are between Moderate Yellow Green, 5GY5/6, and Moderate Olive Green, 5GY4/3. They bear from few to several medium-length large prickles, which are hooked slightly downward, with medium-length, moderately narrow base. There are from few to many small prickles, and both large and small prickles are a color between Strong Brown, 5YR4/5, and Moderate Brown, 5YR3/3. There are no hairs.

The branches are between Moderate Yellow Green, 7.5GY5/7, and Strong Yellow Green, 5GY6/8, in color. They bear from few to several large prickles, which are moderately short to medium-length, hooked slightly downward, with medium-length, moderately narrow base. There are from few to many small prickles, and both small and large prickles are between Dark Greenish Yellow, 7.5Y6/7, and Deep Yellow, 2.5Y6/8, in color, sometimes overlaid with near Dark Red, 5R3/7. There are no hairs, but many stipitate glands.

The new shoots are near Strong Yellowish Green, 5GY7/10, lightly to very heavily overlaid with near Dark Red, 2.5R3/7. They carry few large prickles, and these are short and almost straight to hooked slightly downward, and with short narrow base. There are from few to many small prickles, and both the small and large prickles are near Dark Red, 2.5R3/7. There are no hairs, but many stipitate glands.

I claim:

1. An outdoor bush rose plant of the floribunda class, substantially as herein shown and described, said plant having a vigorous compact habit of growth, with small to medium-size semi-glossy leaves having their lateral margins lifted from the mid-rib, said plant having a tendency to bear numerous blooms, sometimes as many as twenty, on a single stem, the blooms having a light fragrance between tea and spicy, and having a general color effect on freshly opening which is brilliant orange, tending toward yellow orange pink as they mature, and pistils ranging in number from 85 to 140.

No references cited.

ROBERT E. BAGWILL, Primary Examiner